US012672798B2

(12) United States Patent (10) Patent No.: US 12,672,798 B2
Pelssers et al. (45) Date of Patent: Jul. 7, 2026

(54) DETECTION OF BIOMARKERS IN SWEAT

(71) Applicant: KONINKLIJKE PHILIPS N.V.,
Eindhoven (NL)

(72) Inventors: Eduard Gerard Marie Pelssers,
Panningen (NL); **Mark Thomas
Johnson, Arendonk (BE); Thomas
Johannes Van Gijsel, Weert (NL); Ron
Martinus Laurentius Van Lieshout,**
Geldrop (NL); **Kiran Hamilton J.
Dellimore,** Utrecht (NL)

(73) Assignee: KONINKLIJKE PHILIPS N.V.,
Eindhoven (NL)

( * ) Notice: Subject to any disclaimer, the term of this
patent is extended or adjusted under 35
U.S.C. 154(b) by 1218 days.

(21) Appl. No.: 17/602,927

(22) PCT Filed: Apr. 8, 2020

(86) PCT No.: PCT/EP2020/060044
§ 371 (c)(1),
(2) Date: Oct. 11, 2021

(87) PCT Pub. No.: WO2020/208084
PCT Pub. Date: Oct. 15, 2020

(65) Prior Publication Data
US 2022/0175280 A1 Jun. 9, 2022

(30) Foreign Application Priority Data
Apr. 10, 2019 (EP) ..................................... 19168486

(51) Int. Cl.
*A61B 10/00* (2006.01)
*A61B 5/00* (2006.01)
(Continued)

(52) U.S. Cl.
CPC ........ *A61B 5/14517* (2013.01); *A61B 5/4266*
(2013.01); *A61B 10/0064* (2013.01);
(Continued)

(58) Field of Classification Search
None
See application file for complete search history.

(56) References Cited

U.S. PATENT DOCUMENTS 6,454,945 B1 * 9/2002 Weigl .................... B01L 3/5027
422/417
8,712,495 B2 4/2014 Tokita
(Continued)

FOREIGN PATENT DOCUMENTS

JP 61135646 A 6/1986
WO 2007146047 A1 12/2007
(Continued)

OTHER PUBLICATIONS

International Search Report and Written Opinion, International
Application No. PCT/EP2020/060044, Mailed on Jul. 27, 2020.
(Continued)

*Primary Examiner* — Tse W Chen
*Assistant Examiner* — Martin Nathan Ortega

(57) ABSTRACT

There is provided a wearable device for quantitatively
detecting a biomarker in a sweat sample obtained from the
skin of a subject. The wearable device comprises a micro-
fluidic network. The microfluidic network comprises a res-
ervoir filled with a carrier fluid containing a predetermined
amount of a marker; a sample collection chamber disposed
downstream from the reservoir and adapted to contact the
skin of the subject and collect a sweat sample; a first sensor
disposed downstream from the sample collection chamber
(Continued)

and adapted to detect the marker; and a second sensor disposed downstream from the first sensor and adapted to detect the biomarker.

12 Claims, 4 Drawing Sheets

(51) Int. Cl.
    *A61B 5/145*           (2006.01)
    *B01L 3/00*            (2006.01)
(52) U.S. Cl.
    CPC ... *B01L 3/502715* (2013.01); *B01L 2300/047* (2013.01); *B01L 2300/0663* (2013.01); *B01L 2300/069* (2013.01)

(56) References Cited

U.S. PATENT DOCUMENTS

| | | | |
|---|---|---|---|
| 9,675,296 B1 | 6/2017 | Biegelsen | |
| 10,182,795 B2 | 1/2019 | Heikenfeld | |
| 10,888,244 B2 * | 1/2021 | Heikenfeld | A61B 5/0531 |
| 11,064,946 B2 * | 7/2021 | Rogers | A61B 5/6898 |
| 2002/0031836 A1 * | 3/2002 | Feldstein | B01L 3/502738 |
| | | | 422/82.11 |

| | | | |
|---|---|---|---|
| 2006/0205061 A1 * | 9/2006 | Roukes | B01L 3/5027 |
| | | | 435/287.2 |
| 2012/0165626 A1 * | 6/2012 | Irina | A61B 5/14532 |
| | | | 600/362 |
| 2017/0336389 A1 | 11/2017 | Dasgupta | |
| 2018/0136247 A1 | 5/2018 | Boutelle | |
| 2019/0175094 A1 * | 6/2019 | Ortiz | A61B 5/14546 |

FOREIGN PATENT DOCUMENTS

| | | |
|---|---|---|
| WO | 2009025698 A1 | 2/2009 |
| WO | 2012151501 A2 | 11/2012 |
| WO | 2017070641 A1 | 4/2017 |
| WO | 2018006087 A1 | 1/2018 |
| WO | 2018058085 A1 | 3/2018 |
| WO | 2018067412 A1 | 4/2018 |

OTHER PUBLICATIONS

Choi et al., "Advanced Healthcare Materials", vol. 6, No. 5, Mar. 2017.
Xinhua Wang, Victor W.C. Chang and Chuyang Y.Tang. Osmotic membrane bioreactor (OMBR) technology for wastewater treatment and reclamation: Advances, challenges, and prospects for the future. Journal of Membrane Science, vol. 504, Apr. 15, 2016, pp. 113-132.

* cited by examiner

DETECTION OF BIOMARKERS IN SWEAT

This application is the U.S. National Phase application under 35 U.S.C. § 371 of International Application No. PCT/EP2020/060044, filed on 8 Apr. 2020, which claims the benefit of European Application Serial No. 19168486.9, filed 10 Apr. 2019. These applications are hereby incorporated by reference herein.

The disclosure relates to a device, method and system for detecting physiologically relevant biomarkers in a sweat sample obtained from a subject.

BACKGROUND OF THE INVENTION

Non-invasive, continuous and prolonged monitoring of biomarkers that indicate health and well-being is in demand for example for monitoring dehydration, stress, sleep, children's health and in perioperative monitoring. Sweat is a non-obtrusively accessible bio-fluid containing physiologically and metabolically rich information. Some examples of clinical relevant components of sweat are Na+, Cl− and/or K+ to monitor dehydration, lactate as an early warning for inflammation (relevant to sepsis), glucose for diabetics & neonates, and cortisol for monitoring sleep and stress.

WO 2007/146047 A1 discloses patches, systems, and methods for measuring glucose.

Adult humans produce heat in the order of 100 Joule per second (100 Watt) when at rest. For a person wearing clothes at a temperature of around 22° C. this heat is removed by passive means such as losing heat conduction and convection. In this case, the core temperature remains constant. However, when i) a person starts to conduct labor or exercise and/or ii) the ambient temperature is increasing the noted means are insufficient to maintain the core temperature. To maintain homeostasis, the body induces dilation of blood vessels in the skin to cool the blood and starts to produce sweat which by evaporation cools the skin.

The amount of sweat produced by persons at ambient temperature with only light exercise or light labor is rather low, with a typical value of about 0.3 nL/min/gland (values measured between zero and 0.7 nL/min/gland). When persons are at rest but at an elevated temperature of 36° C., the sweat production rate is on average $0.36 \text{ mg*cm}^{-2}\text{*min}^{-1}$. When assuming 2.03 million sweat glands per 1.8 m$^2$ (skin area of standardized person) and sweat density of 1 g/mL the average sweat production is about 3.2 nanoliter per gland per min (nL/gland/min). Due to the elevated temperature above the thermal neutral zone the body requires cooling and so the sweat production rate is increased. Sweat rate may also be increased by stimulation of the skin.

A major problem in analyzing sweat in a semi-continuous manner is that the time between sweat release to the skin and actual sensing of a biomarker in this sweat aliquot can be very long. This time delay is caused by the fact the sweat production can be very low and consequently the time between sweat entering a microfluidic device and reaching the sensor is rather, long up to hours. For example, this time delay can be more than 24 hours depending on the device. One can consider decreasing the height and/or width of the channels of a wearable device, however, these are generally already only in the order of 100 micron and further decreasing channel dimensions will increase the complexity of the microfabrication.

Another problem is that besides sweat secretion there is Trans Epidermal Water Loss (TEWL), which is water evaporation from the skin. This water evaporation may play a role in collection chambers as well due to condensation and especially at low sweat-rates may give an unknown dilution of the sweat. Still another problem is that constituents on the skin may dissolve in the small volumes of sweat and have a disturbing influence on the correct measurement of a biomarker concentration.

Systems and devices, for example wearable fluidic sampling devices, for qualitatively or quantitatively detecting biomarkers in sweat are known in the art. Examples include those described in Gao et al., Nature 529, 509-514 (2016), Choi et al., Adv. Healthcare Mater. 2017, 6, 1601355, and Koh et al., Sci. Transl. Med. 8, 3664a165 (2016). Such devices typically require the subject to be exercising or to be exposed to elevated temperatures in order to collect enough sweat for analysis. The development of reliable sweat sensing and devices thereto has been hampered by several issues: (1) results from sweat sensing have been highly variable; (2) the correlation between blood and sweat values appears to be lacking for various biomarkers; (3) the focus of sweat sensing has been on sensors in such devices, not on reliable and robust collection methods for the minute amounts produced.

The time to transport (via a fluidic structure) sweat from the skin to a sensor can be rather long up to hours. Obviously, one can increase the sweat rate by exercise, by increasing the ambient temperature or stimulating the skin; however, this is not practical if there is a desire to measure biomarker concentration of ill persons or patients recovering in the general ward or to monitor persons conducting daily routines.

SUMMARY OF THE INVENTION

As noted above, the limitations with existing devices and methods is that the existing techniques either require a subject to be exercising or to be at elevated temperatures in order to produce enough sweat, which can be inconvenient and uncomfortable for the subject, as well as being potentially detrimental to the wellbeing of the subject. The existing devices and methods can also require a long time to transport sweat from the skin to the sensor, and are thus impractical for real-time clinical application. It would thus be valuable to have an improvement aimed at addressing these limitations. The invention is defined by the independent claims. The dependent claims define advantageous embodiments.

Therefore, according to a first aspect, there is provided a device for quantitatively detecting a biomarker in a sweat sample obtained from the skin of a subject, the device comprising:

a microfluidic network, the microfluidic network comprising:

a reservoir filled with a carrier fluid containing a predetermined amount of a marker;

a sample collection chamber disposed downstream from the reservoir and adapted to contact the skin of the subject and collect a sweat sample;

a first sensor disposed downstream from the sample collection chamber and adapted to detect the marker; and a second sensor disposed downstream from the first sensor and adapted to detect the biomarker.

By the use of an artificial marker in the carrier fluid (artificial being defined as not being present in sweat) the dilution factor of sweat by the carrier fluid can be determined by a first sensor measuring solely the concentration of this marker. As such, this construct enables timely measurement of a biomarker concentration in sweat by the second sensor.

In addition, on the basis of the known flow rate of the carrier fluid, the flow rate of the sweat can be calculated from the measured concentration of this marker, which is relevant since the concentration of particular biomarkers in sweat depends on the average sweat flow rate per gland.

According to the invention, the first sensor is adapted to measure concentration of the marker in the carrier fluid.

In some embodiments, the microfluidic network comprises one or more additional sensors disposed downstream from the first sensor, each of the one or more additional sensors adapted to detect a different biomarker.

In some embodiments, the device is configured to detect the biomarker at a sweat flow rate of between 0.03 and 20 nL/min/gland. In some embodiments, the device is configured to detect the biomarker at a sweat flow rate of between 0.03 and 0.7 nL/min/gland.

In some embodiments, a membrane which is selective for the biomarker is disposed downstream from the sample collection chamber and upstream of the sensors.

In some embodiments, the microfluidic network further comprises a recirculation channel extending from a section of the microfluidic network downstream from the first and second sensors to a section of the microfluidic network intermediate the reservoir and the sample collection chamber.

In some embodiments, the marker comprises a dye, an inert colloidal particle, or an electrochemically detectable compound of predetermined concentration. In some embodiments, the dye may be a fluorescent dye.

In some embodiments, the device further comprises one or more pumps configured to pump the carrier fluid at a predetermined flow rate of from 10 nL/min to 60 nL/min. In some embodiments, the device further comprises one or more pumps configured to pump the carrier fluid at a predetermined flow rate of 30 nL/min.

According to a second aspect, there is provided a method of quantitatively detecting a biomarker in a sweat sample from a subject using a wearable device in contact with the skin of the subject, the method comprising:

pumping carrier fluid containing a predetermined amount of a marker to a sample collection chamber of the wearable device, wherein the sample collection chamber is adapted to contact the skin of the subject and collect a sweat sample;

pumping the carrier fluid containing the marker and the sweat sample from the sample collection chamber to first and second sensors;

acquiring data relating to the marker present in the carrier fluid from the first sensor;

acquiring data relating to the biomarker from the second sensor; and determining the concentration of the biomarker in the sweat sample based on the data from the first and second sensors.

According to the invention, the method comprises acquiring data relating to the concentration of the marker in the carrier fluid from the first sensor;

determining the flow rate of one or both of the carrier fluid and the sweat sample based on the acquired data from the first sensor.

In some embodiments, the method comprises determining the concentration of the biomarker in the sweat sample based on the flow rate of one or both of the carrier fluid and the sweat sample.

In some embodiments, the biomarker comprises one or more of: Na+, K+, Cl−, urea, ethanol, glucose, lactate ions, ammonium ions or cortisol.

In some embodiments, the method comprises acquiring physiological data on the subject from a physiological sensor; and adjusting the flow rate of the carrier fluid based on the acquired physiological data.

According to a third aspect, there is provided a system for quantitatively detecting a biomarker in a sweat sample obtained from the skin of a subject, comprising:

a wearable device as described herein; and a processor configured to:

acquire data from the first sensor of the wearable device, wherein the data acquired from the first sensor comprises concentration of the marker in the carrier fluid;

acquire data from the second sensor of the wearable device; and determine the concentration of the biomarker in the sweat sample based on the data from the first and second sensors.

In some embodiments, the processor is configured to determine sweat flow rate based on the concentration of the marker in the carrier fluid.

According to a fourth aspect, there is provided a computer program product comprising a computer readable medium. The computer readable medium has computer readable code embodied therein. The computer readable code is configured such that, on execution by a suitable computer or processor, the computer or processor is caused to perform the method described earlier.

According to the aspects and embodiments described above, the limitations of existing techniques are addressed. In particular, according to the above-described aspects and embodiments, the amount of a biomarker in a sweat sample from a subject can be reliably and quickly detected without requiring the subject to be exercising heavily or being at elevated temperatures. In particular, the subject can be carrying out only light exercise (such as rehabilitation, or even just walking), or be exposed to only a slight elevation in temperature and the amount of a biomarker in the subject's sweat can be determined despite the relatively low sweat rate. The aspects and embodiments described above are also suited to subjects who are completely at rest at room temperature despite having a very low sweat rate. The detection of biomarker concentration according to the above-described aspects and embodiments is convenient, comfortable, and non-invasive for the subject. The use of the carrier fluid in the device allows for a quicker and more efficient collection of sweat samples, even though the sweat sample may be a small quantity of liquid, and also prevents evaporation of sweat before analysis. The biomarker concentration in sweat is determined based on a dilution factor (dilution of carrier fluid by sweat) from the data obtained from the first sensor. There is thus provided an improved device, method and system for quantitatively detecting a biomarker in a sweat sample obtained from the skin of a subject.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

As noted above, there is provided herein an improved device, system and method for quantitatively detecting a biomarker in a sweat sample obtained from the skin of a subject. The device can be configured to be worn by a subject. Thus, the device can be a wearable device.

In some embodiments, the device may comprise a strap (or band) for placement around a part of the body of the subject, such that the device can be worn at a location suitable for receiving a sample of sweat from the subject. In some embodiments, an adhesive layer is provided on the underside of the device for fixation of the device to the skin of the subject.

The device may be configured to be worn by a subject at any location on the body of the subject suitable for collecting sweat samples. In some embodiments, the location may be a location comprising bone close to the skin surface (e.g. to ensure a well-defined contact with the skin). For example, in some embodiments, the device can be configured to be worn on an arm (upper or lower) of the subject, a wrist or finger of a subject, a forehead of a subject, or any other location on the body of the subject suitable for collecting a sweat sample.

The subject can be any type of subject (e.g. a patient or any other subject). The device can be for use by a trained user, such as a medical professional (e.g. a doctor, a nurse, or any other medical professional) or an untrained user (e.g. the subject themselves, a care giver, a family member, or any other untrained user). The device can be for use in a medical environment (e.g. a hospital, a surgery, or any other medical environment) and/or non-medical environment (e.g. at home, or any other non-medical environment).

Figure 1:
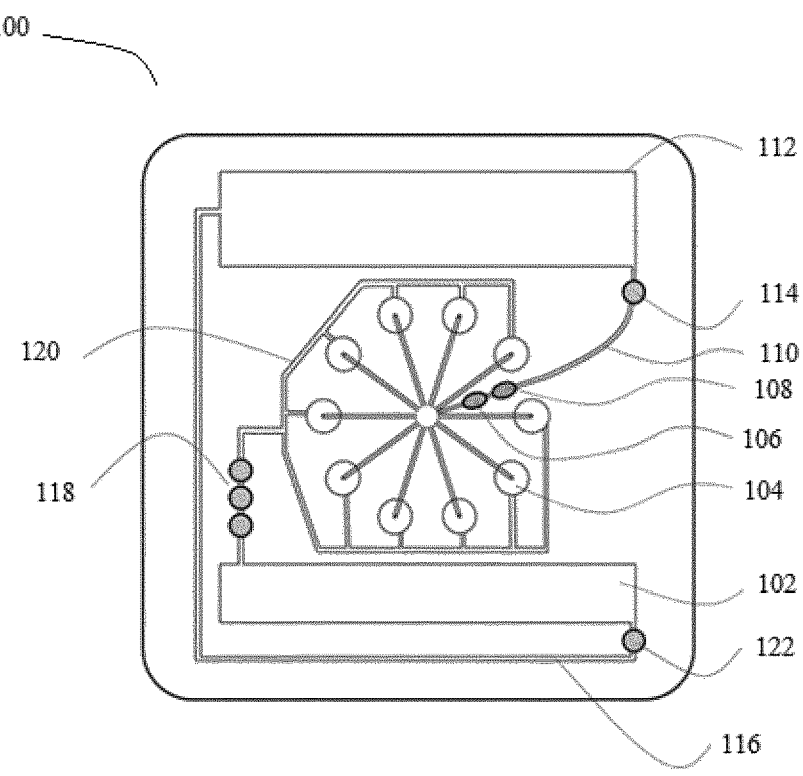
FIG. 1 depicts a device according to an embodiment.

FIG. 1 illustrates a device 100 for quantitatively detecting a biomarker in a sweat sample from a subject according to an embodiment. As illustrated in FIG. 1, the device 100 comprises a microfluidic network. The microfluidic network is shown with certain components, each of which will be described in turn below. However, it will be understood that the device may comprise other components which are not depicted in FIG. 1, such as other flow channels, pumps or valves in the microfluidic network, or microelectronic circuitry. Similarly, electrical wires powering the pump(s), the actuators of the pump(s), wires connecting the sensors, ADC's, electronic logic circuit and electronics communicating to the outside world (with wires or wireless) are not drawn.

Methods of constructing such wearable devices containing flexible microfluidic networks provided with sensors and flexible microelectronic circuitry are known in the art, such as is described in Gao et al., Nature 529, 509-514 (2016).

As illustrated in FIG. 1, the microfluidic network of device 100 comprises a reservoir 102, pre-filled with a carrier fluid containing a marker of known (i.e. predetermined) concentration; a sample collection chamber 104 disposed downstream from the reservoir and adapted to contact the skin of the subject and collect a sweat sample; a first sensor 106 disposed downstream from the sample collection chamber 104 and adapted to detect the marker;

and a second sensor 108 disposed downstream from the first sensor 104 and adapted to detect the biomarker.

Reservoir 102 may be pre-filled with a known volume of carrier fluid. The carrier fluid may be any inert liquid, for example an aqueous liquid or an organic solvent. In one embodiment, the carrier fluid is an aqueous fluid to ensure miscibility with the collected sweat sample and good solvation of any biomarker present in the collected sweat sample. An additional benefit of using a carrier fluid is the fact that TEWL, which is water evaporation of the skin, does not occur in a sample collection chamber of the device due to complete wetting. Consequently, there can be no dilution of the sweat by the TEWL. In some embodiments, reservoir 102 may be dimensioned so as to hold sufficient carrier fluid for the intended usage lifetime of device 100. For example, for an intended usage of three days, with a carrier fluid flow rate of 30 nL/min, reservoir 102 may be dimensioned so as to hold 150 μL carrier fluid.

The wearable device described herein also includes a sample collection chamber, denoted as 104 in FIG. 1. In the embodiment of FIG. 1, a plurality of sample collection chambers is present, connected in parallel and provided with carrier fluid via manifold 120. The position and size of each of the plurality of sample collection chambers may be selected depending on a number of factors. In one embodiment, each of the plurality of sample collection chambers is dimensioned and positioned within the device so as to be located over at least one sweat gland on the subject wearing the wearable device. The sample collection chamber 104 is disposed downstream of the reservoir and adapted to contact the skin of the subject and collect a sweat sample. In one embodiment, the sample collection chamber may comprise an opening or port on the underside of the device, and forms a close contact with the skin of the subject. In this way, and by virtue of the flow of the carrier fluid within the microfluidic network, any sweat sample produced on the surface of the skin adjacent sample collection chamber 104 can be drawn into the microfluidic network of the device by capillary action.

As is seen in FIG. 1, a triple valve pump 118 is disposed between reservoir 102 and sample collection chamber 104. Triple valve combinations of this type are known in the art, with each valve being independently operable from the other valves. Operation of the three valves of pump 118 in this way generates a flow of carrier fluid within the microfluidic network.

Downstream from sample collection chamber 104 are first sensor 106 and second sensor 108. First sensor 106 is adapted to detect the marker present in the carrier fluid, while second sensor 108 is adapted to detect a biomarker present in the sweat sample (and so present in the carrier fluid).

The marker may be any detectable marker which is soluble in the carrier fluid and detectable by, for example, electrical or optical sensing principles. For example, the marker may be a colloid marker comprising colloidal particles, such as polystyrene particles (which could be coated with a moiety such as bovine serum albumin), colloidal carbon or gold, or detectable latex microspheres. Inert colloidal particles can be detected, and their concentration (for example number of particles per volume) determined using a wide variety of known sensors and techniques, including (light) scattering, fluorescence, electrical impedance and optically using a camera. For example, a light beam, generated by a LED, crossing the fluidic channel, can conduct such optical sensing. At the opposite site, an optical detector is placed which measures the light absorption as a measure of the particle concentration. The marker may be a dye, for example a fluorescent dye such as fluorescein, rhodamine or any other dye which is soluble in the carrier fluid. Dyes are well known in the art and are known to have particular absorbances and/or emissions at specific wavelengths of light, rendering them ideal for electromagnetic detection. The marker may be a chemical compound having particular properties that render it detectable and its concentration measurable, for example by the compound generating a signal on an electrochemical based sensor. It is well within the wherewithal of the skilled person to select a detectable marker and provide a sensor which is sensitive and/or specific to that marker. According to the invention, the first sensor 106 is adapted to measure concentration of the marker in the carrier fluid, using any of the above mentioned well established techniques.

The marker is present in the carrier fluid in a predetermined concentration. By using a predetermined concentration of marker, it becomes possible to monitor any change in concentration of the marker over time as a result of the carrier fluid being diluted by the sweat sample. In turn, this allows for the determination of the sweat flow rate and the concentration of any biomarker present in the sweat sample. The concentration of biomarkers in sweat is known to depend on the average sweat flow rate per gland and so having knowledge of the sweat flow rate allows for a more accurate diagnosis.

Second sensor 108 is adapted to detect the presence of the biomarker in the carrier fluid, by virtue of the sweat sample having been taken up by the carrier fluid in sample collection chamber 104. In some embodiments, the biomarker comprises or is selected from one or more of: Na+, K+, Cl−, urea, ethanol, glucose, lactate ions, ammonium ions or cortisol. Biosensors for detecting each of these are known in the art, as described for example in Gao et al., Nature 529, 509-514 (2016) and can be configured for wireless transmission of data to an external processor, if desired.

In some embodiments, the device is configured to detect the biomarker at a sweat flow rate of between 0.03 and 20 nL/min/gland. For example, in some embodiments, the device may detect the biomarker at a sweat flow rate of between 0.03 and 0.7 nL/min/gland, which corresponds to typical sweat flow rates for subjects in a sedentary state. The term sedentary state will be understood as meaning that the subject is carrying out light exercise (for example rehabilitation), light labour (for example walking) and/or having a slightly elevated body temperature. In some embodiments, the device may be configured to detect the biomarker at a sweat flow rate of between 5 and 20 nL/min/gland, which corresponds to typical sweat flow rates for subjects carrying out more strenuous exercise or manual labor.

At a sweat rate of 0.03 nL/min/gland, and take up of sweat from ten sweat glands, the total sweat rate will be 0.3 nL/min. This constitutes a ~1% dilution when the carrier fluid flow rate is set to 30 nL/min. Consequently, the time from sampling sweat of the skin to actual sensing is reduced from ~27 hours to about 16 minutes. This is an appropriate amount of time to detect clinically relevant changes in biomarkers at early stage. Assuming a maximum sweat rate of 20 nL/min/gland (heavy exercise), the total sweat rate will be 200 nL/min and in this case the dilution of the carrier fluid will be a factor of ~7.7. Therefore, when the undiluted carrier fluid would constitute a signal of about 4000 levels, the diluted signal would be about 535 levels, which can still be measured accurately by first sensor 106. In the latter case, the time from sampling sweat of the skin to actual sensing would be about 2 minutes. Thus, in some embodiment, pump 118 is operable to pump the carrier fluid at a predetermined flow rate of from 10 nL/min to 60 nL/min. In some embodiments, pump 118 is operable to pump the carrier fluid at a predetermined flow rate of 30 nL/min.

In some embodiments (not illustrated), the microfluidic network comprises one or more additional sensors disposed downstream from the first sensor, each of the one or more additional sensors adapted to detect a different biomarker.

In a wearable device as described herein, for example such as in the embodiment of FIG. 1, downstream of first sensor 106 and second sensor 108 is an exit channel 110 leading to waste chamber 112. Waste chamber 112 may be dimensioned based on the intended usage of the device (for example three days), the flow rate of carrier fluid being pumped through the device during use and an average sweat rate. For example, waste chamber 112 may be dimensioned so as to hold at least 225 µL of fluid. Valve 114 in exit channel 110 controls flow of carrier fluid (containing the sweat sample) so that, if required, the carrier fluid has a longer residence time in the vicinity of the sensors. Completing the microfluidic network of wearable device 100 is air-line 116, controlled by valve 122 and provided to pressure-equalize the microfluidic network in view of the flow of carrier fluid from reservoir 102 to waste chamber 112.

In use, and after fixation of device 100 to the skin of a subject, triple valve pump 118 is activated and starts to transport carrier fluid from reservoir 102 toward sample collection chamber 104 via the microfluidic manifold 120. To allow air to replace the carrier fluid in reservoir 102, to prevent a vacuum, valve 122 located in air-line 116 is opened and at the same time, valve 114 in exit channel 110 is opened. Subsequently the carrier fluid flows over the skin located in sample collection chamber(s) 104 thereby taking up produced sweat. Thereafter, the carrier fluid migrates further, reaching first sensor 106 and second sensor 108, before entering waste chamber 112.

In some embodiments, device 100 further comprises microelectronic components that receive one or more signals from one or both of first sensor 106 and second sensor 108. For example, device 100 may comprise one or more Analog-to-Digital Converters (ADC) to transform a received analogue signal and transform it to a digital signal to reduce noise and make the signal more accessible to a processor of a system such as may be described herein. With a sufficiently accurate ADC (for instance 12-bit), 4096 levels are available to cover the dynamic range. When the carrier fluid is diluted by 1% there are ample levels available (~40) to record this change via the concentration measurement by first sensor 106. With a noise in the order of 40 levels, there is sufficient precision to distinguish a change of 2%. Therefore, the noise should be about 1% or smaller which is achievable with the above-mentioned sensing principles.

Figure 2:
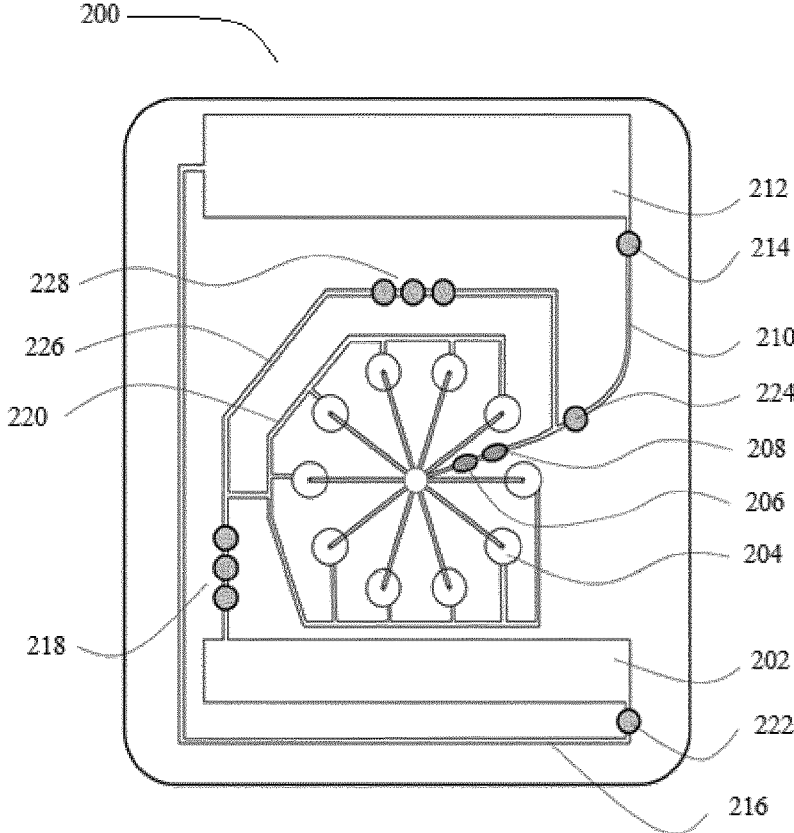
FIG. 2 depicts a device according to an embodiment.

FIG. 2 illustrates a further device 200 for quantitatively detecting a biomarker in a sweat sample from a subject according to an embodiment. Device 200 has a number of like-for-like features when compared with the device of FIG. 1, as will be noted from the explanation below. It will be understood that discussion of these like-for-like features, including, for example, the nature of the carrier fluid or the sensors, in connection with the embodiment of FIG. 1 are equally applicable to the embodiment of FIG. 2, and so will not be repeated.

As illustrated in FIG. 2, the microfluidic network of device 200 comprises a reservoir 202, again pre-filled with a carrier fluid containing a marker of known (i.e. predetermined) concentration; a sample collection chamber 204 disposed downstream from the reservoir and adapted to contact the skin of the subject and collect a sweat sample; a first sensor 206 disposed downstream from the sample collection chamber 204 and adapted to detect the marker; and a second sensor 208 disposed downstream from the first sensor 204 and adapted to detect the biomarker.

As with the embodiment of FIG. 1, a plurality of sample collection chambers are present in wearable device 200, connected in parallel and provided with carrier fluid via manifold 220. As is seen in FIG. 2, a triple valve pump 218 is disposed between reservoir 202 and sample collection chamber 204. Downstream from sample collection chamber 204 are first sensor 206 and second sensor 208, corresponding to first sensor 106 and second sensor 108 of the embodiment of FIG. 1 respectively.

In the embodiment of FIG. 2, downstream of first sensor 206 and second sensor 208 is an exit channel 210 leading to waste chamber 212. Valve 214 in exit channel 210 controls flow of carrier fluid (containing the sweat sample) so that, if required, the carrier fluid has a longer residence time in the vicinity of the sensors. The embodiment of FIG. 2 also includes a recirculation channel extending from a section of the microfluidic network downstream from the first and second sensors to a section of the microfluidic network intermediate the reservoir and the sample collection chamber, with access to the recirculation channel being controlled by an additional valve 224 in exit channel 210. Closure of valve 224 prevents carrier fluid flowing to waste chamber 212 and diverts it into the recirculation channel in the form of additional shunt flow path 226, provided with triple valve pump 228. Shunt flow path 226 rejoins the microfluidic network upstream of the sample collection chamber(s) 204 but downstream of reservoir 202 and triple valve pump 218. This embodiment is advantageous as it permits recirculation of the carrier fluid through sample collection chamber 204, thereby collecting multiple sweat samples and increasing the relative concentrations of biomarkers in the carrier fluid as it passes second sensor 208. Besides timely arrival of sweat at the sensors and improved mixing, a marker in the fluid has more chance to bind to the sensor due to passing the sensor several times, which enhances the detection limit. In operation, the carrier fluid fills the main flow path and the additional shunt 226 (the pump 218 in the shunt) is set on open where after the main flow path is temporarily interrupted by closure of valve 224 positioned after the sensors 206 and 208 and 2) by simultaneously setting pump 218 in the main flow in a closed configuration. Next, pump 228 in shunt 226 creates a recirculation between sensors 206 and 208 and sample collection chambers 204, typically for a few minutes. In order to accommodate the extra volume of multiple sweat samples, shunt flow path 226 may be formed within a flexible or compliant material, thus providing it with flexible elastic inner surfaces. Completing the microfluidic network of wearable device 200 is air-line 216, controlled by valve 222 and provided to pressure-equalize the network in view of the flow of carrier fluid from reservoir 202 to waste chamber 212.

Figure 3:
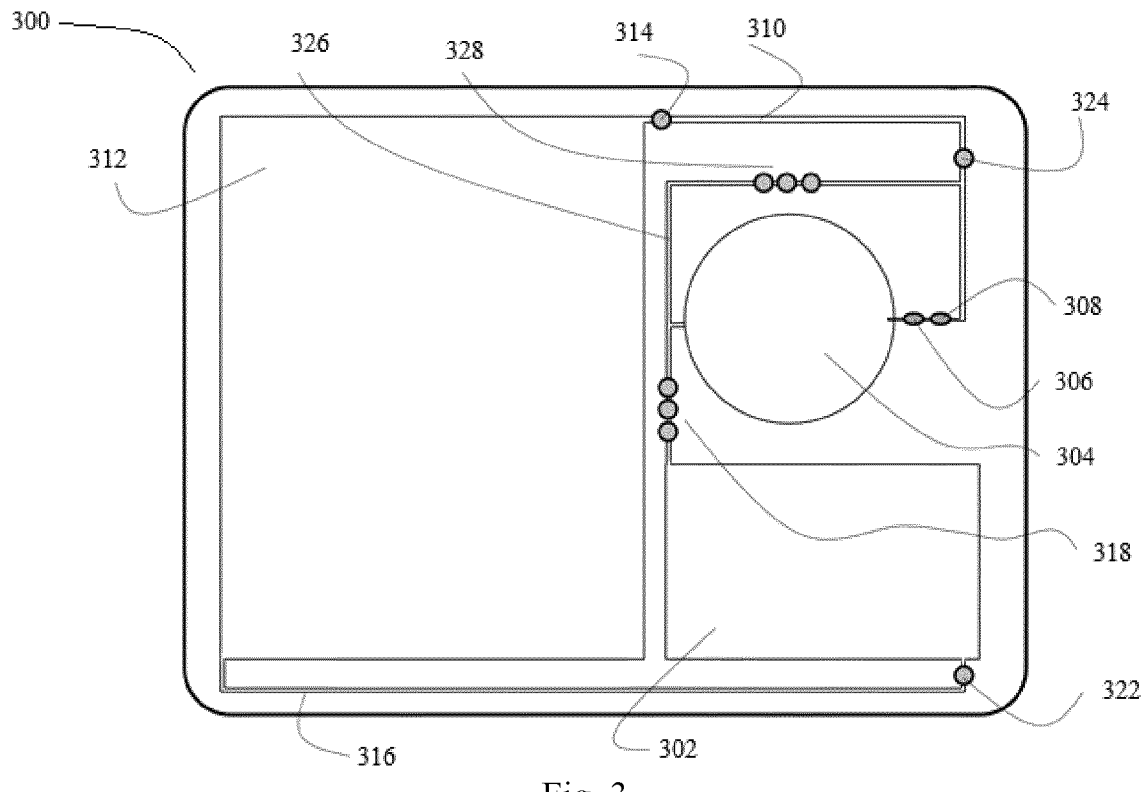
FIG. 3 depicts a device according to an embodiment.

FIG. 3 illustrates a further wearable device 300 for quantitatively detecting a biomarker in a sweat sample from a subject according to an embodiment. Device 300 has a number of like-for-like features when compared with the devices of FIGS. 1 and 2, as will be noted from the explanation below. It will be understood that discussion of these like-for-like features, including, for example, the nature of the carrier fluid or the sensors, in connection with the embodiment of FIGS. 1 and 2 are equally applicable to the embodiment of FIG. 3, and so will not be repeated.

As illustrated in FIG. 3, the microfluidic network of device 300 comprises a reservoir 302, again pre-filled with a carrier fluid containing a marker of known (i.e. predetermined) concentration; a sample collection chamber 304 disposed downstream from the reservoir and adapted to contact the skin of the subject and collect a sweat sample; a first sensor 306 disposed downstream from the sample collection chamber 304 and adapted to detect the marker; and a second sensor 308 disposed downstream from the first sensor 304 and adapted to detect the biomarker.

In the embodiment of FIG. 3, downstream of first sensor 306 and second sensor 308 is an exit channel 310 leading to waste chamber 312. Valve 314 in exit channel 310 controls flow of carrier fluid (containing the sweat sample) so that, if required, the carrier fluid has a longer residence time in the vicinity of the sensors. As with the embodiment of FIG. 2, the embodiment of FIG. 3 also includes an additional valve 324 in exit channel 310. Closure of valve 324 prevents carrier fluid flowing to waste chamber 312 and diverts it into an additional shunt flow path 326, provided with triple valve pump 328, which can be operated as described above. Shunt flow path 326 rejoins the microfluidic network upstream of the sample collection chamber 304 but downstream of reservoir 302 and triple valve pump 318, to permit recirculation of the carrier fluid as described previously. Completing the microfluidic network of wearable device 300 is air-line 316, controlled by valve 322 and provided to pressure-equalize the network in view of the flow of carrier fluid from reservoir 302 to waste chamber 312.

The embodiment of FIG. 3 differs from those of FIGS. 1 and 2, in that a single large sample collection chamber 304 is provided, instead of the plurality of small sample collection chambers seen in FIGS. 1 and 2. In this embodiment, sample collection chamber 304 has a surface area of approximately one square centimeter, having a diameter of approximately 11 mm. Sample collection chamber 304 has an internal height in the order of 100 μm, giving an internal volume of approximately 7000 nL, far exceeding the volume of the microfluidic channels of the network.

A typical sweat flow rate can range from extremely low (0.03 nL/min/gland) to high at intensive exercise (20 nL/min/gland but in average 5.2 nL/min/gland over 24 hours). Furthermore, on average, there are approximately 100 active sweat glands per square centimetre of skin, and so by utilizing larger collection chambers such as sample collection chamber 304 the average sweat flow rate ranges from 3 to 520 nL/min. Consequently, without carrier fluid the filling times would range from about 39 hours to 13.5 minutes. Again, for the low sweat flow rates this is unacceptable. By using a carrier fluid as described, with a carrier fluid flow rate of 300 nL/min the filling times for sample collection chamber 304 would range from 23 minutes to 8.6 minutes. Again, with a use of 72 hours, the maximum volume that the waste area has to accommodate is about 3.5 mL. In this case, the dimensions of a typical waste area will be about 2.3 cm in length (horizontal in FIG. 3), 3 cm in width (vertical in FIG. 3) and 5 mm in height (not drawn in FIG. 3). To enable efficient mixing a recirculation loop is shown as additional shunt flow path 326 in the embodiment depicted in FIG. 3.

Figure 4:
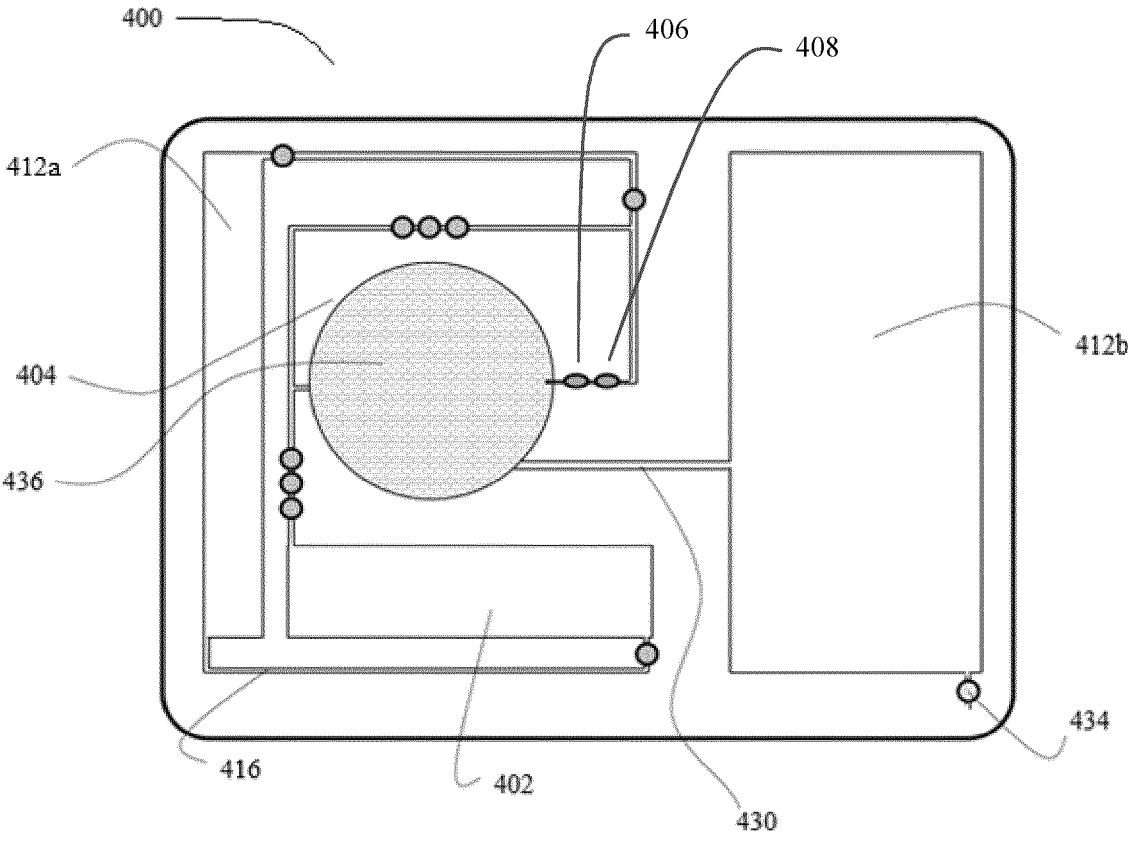
FIG. 4 depicts a device according to an embodiment.

FIG. 4 illustrates a further wearable device 400 for quantitatively detecting a biomarker in a sweat sample from a subject according to an embodiment. Device 400 has a number of like-for-like features when compared with the previously described embodiments and it will be understood that discussion of these like-for-like features, including, for example, the nature of the carrier fluid or the sensors, in connection with those embodiments are equally applicable to the embodiment of FIG. 4, and so will not be repeated.

In the embodiment of FIG. 4, a membrane 436 which is selective for the biomarker is disposed downstream from the sample collection chamber 404 and upstream of first and second sensors 406 and 408. In other words, the microfluidic flow path from reservoir 402 to first and second sensors 406 and 408 is separated from the sample collection chamber 404 by membrane 436. The membrane 436 prevents disturbing constituents from entering the carrier fluid, such as other biomarkers, sebum and constituents on the skin while still have allowing for a sufficiently fast filling time. As such, the measurement of the desired biomarker by the second sensor can be carried out in the carrier fluid without the disturbing influences, thereby increasing the specificity of the measurement. In this case, after filling, the carrier fluid remains in the circular loop and the concentration of the desired biomarker that passes the membrane 436 is gradually increased in the carrier fluid. Some additional liquid may enter the recirculating carrier fluid, which is accommodated by an elastic part in the recirculation channels (not drawn). The membrane 436 may have the following functions: size exclusion, selective for hydrophilic or hydrophobic constituents and/or selective for ions (for instance an osmosis membrane).

In addition to a recirculation loop and exit channel as in the embodiments of FIGS. 2 and 3, the device of FIG. 4 is provided with waste chamber 412a, which in this embodiment is for collecting carrier fluid only. Waste chamber 412a is provided with a pressure-equalizing air-line 416 back to reservoir 402, and is of a smaller volume than those of previously described embodiments, to ensure that the recirculation loop/shunt flow path is filled as much as possible. Device 400 is also provided with sweat overflow channel 430, leading to sweat waste chamber 412b, provided with air-vent 434. Air-vent 434 may be formed, for example, from a hydrophobic membrane. The entry point to sweat overflow channel 430 is from sample collection chamber 404, and so upstream of membrane 436. In some embodiments sweat waste chamber 412b may be omitted if the sweat collected under membrane 436 is limited and the microfluidic volume increase is accommodated by an elastically deformable membrane and an elastically deformable inner surface of the recirculation loop.

Figure 5:
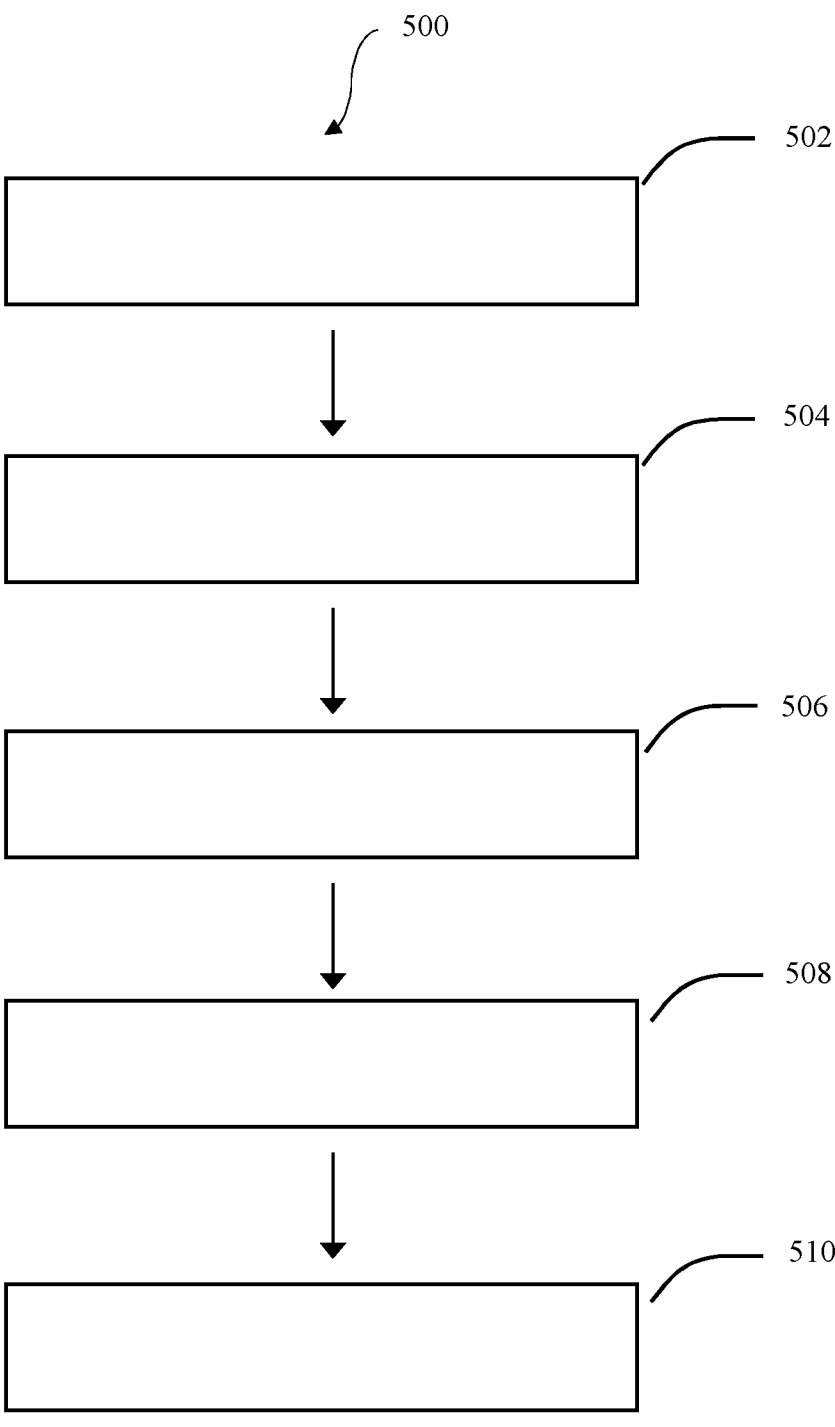
FIG. 5 is a flow chart illustrating a method according to an embodiment.

FIG. 5 is a flow chart illustrating a method 500 for quantitatively detecting a biomarker in a sweat sample from a subject using a wearable device in contact with the skin of the subject. The wearable device may be any wearable device as described herein, for example with reference to FIGS. 1 to 4. At block 502, a carrier fluid containing a predetermined amount of a marker is pumped to a sample collection chamber of the wearable device, wherein the sample collection chamber is adapted to contact the skin of the subject and collect a sweat sample. At block 504, the carrier fluid containing the marker and the sweat sample is pumped from the sample collection chamber to first and second sensors, which may be on the wearable device. At block 506, data relating to concentration of the marker present in the carrier fluid is acquired from the first sensor. At block 508, data relating to the biomarker from the second sensor is acquired. At block 510, the concentration of the biomarker in the sweat sample is determined based on the data from the first and second sensors.

In some embodiments, the method may comprise shutting off flow of carrier fluid (and sweat sample) to a waste chamber, and recirculating carrier fluid (and sweat sample) to the sample collection chamber and first and second sensors.

In some examples, the method may comprise operating an electro-wetting protocol in or proximal to the sample collection chamber to facilitate collection of sweat samples.

In some embodiments, the method determines the flow rate of one or both of the carrier fluid and the sweat sample based on the acquired data from the first sensor. In some embodiments, the concentration of the biomarker in the sweat sample is determined based on the flow rate of one or both of the carrier fluid and the sweat sample.

In some embodiments, the method may comprise determining a sweat dilution factor, from which the sweat flow rate can be determined. The sweat flow rate is relevant since for particular biomarkers the concentration in sweat as measured by the second sensor depends on the average sweat rate per gland. Consequently, via a look up table one can establish if the measured biomarker concentration is caused by an illness or just by a change in sweat rate.

The sweat dilution factor Ds can be determined via:

$$Ds = 1/(1 - Cm/Cr) \qquad \text{Eq. 1}$$

where Cm is the concentration of the marker as measured by the first sensor and Cr is the a priori predetermined concentration of the marker in the undiluted carrier fluid.

It will be apparent that the concentration of biomarker in the undiluted sweat sample (i.e. the clinically relevant concentration which allows a diagnosis to be made) can be derived from the measured concentration of this biomarker in the combined carrier fluid and sweat sample using the sweat dilution factor.

In addition, the total sweat flow rate Qs (volume per time unit) can be determined via:

$$Qs = [1/(Ds - 1)] * Qc \qquad \text{Eq. 2}$$

where Qs is generated by the pumping action of sweat glands and Qc is the known set flow rate of the carrier fluid generated by the pumping action of a pump.

Furthermore, the time delay $\Delta T$ between skin sampling and actual measurement of a sweat aliquot, is defined via:

$$\Delta T = V/(Qs + Qc) \qquad \text{Eq. 3}$$

Where V is the volume of the microfluidic structure.

In some embodiments, the method may comprise controlling one or more pumps in the microfluidic network to pump the carrier fluid at a predetermined flow rate of from 10 to 60 nL/min. In some examples, the pump may be configured to pump the carrier fluid at a predetermined flow rate of from 20 to 50 nL/min, for example from 25 to 40 nL/min, for example about 30 nL/min.

In some embodiments (not depicted), the method may comprise acquiring physiological data on the subject from a physiological sensor; and adjusting the flow rate of the carrier fluid based on the acquired physiological data. Examples of such physiological sensors include heart rate monitors, blood pressure monitors, thermometers or temperature probes, or any other physiological sensor as is known in the art.

In some embodiments, the method may comprise adapting the flow rate of the carrier fluid on the basis of the volume of sweat excreted. As noted previously there can be as much as a 2 to 3 order of magnitude difference in sweat production from ~0.03 to ~20 nL/min/gland. In the latter case, it is clear that there is no need for dilution since sufficient sweat is excreted (200 nL/min) to allow sweat analysis in a reasonable period. In this embodiment the volume of the carrier fluid (i.e., diluent) added to the sweat is adapted according to the volume of sweat excreted, based on the physiological sensor measurement. This can be achieved by controlling the operation of the triple valve pump disposed between the reservoir and the sample collection chamber based on the physiological sensor measurement. The physiological sensor may be any one of the following: i) an inertial sensor such as an accelerometer which measures the activity level and intensity of activity of the individual, ii) a pH sensor which measures the sweat pH which is known to increase with increasing sweat rate, iii) a vital signs sensor such as a PhotoPlethysmoGram (PPG) sensor which measures the heart rate and respiration rate of the individual, and iv) a sweat flow rate sensor. In all cases, if intense activity is detected the volume of the carrier fluid flow rate is dynamically decreased by control of the triple pump valve. The reduction in the flow rate of the carrier fluid can be scaled inversely with increased sweat excretion rate. The key advantages of this embodiment are twofold: i) it prevents the unnecessary depletion of diluent in situations when sweat dilution is not needed, which will extend the lifetime of the patch; ii) it will allow the reservoirs for the diluent and waste fluid to be smaller allowing for a more compact patch design.

Figure 6:
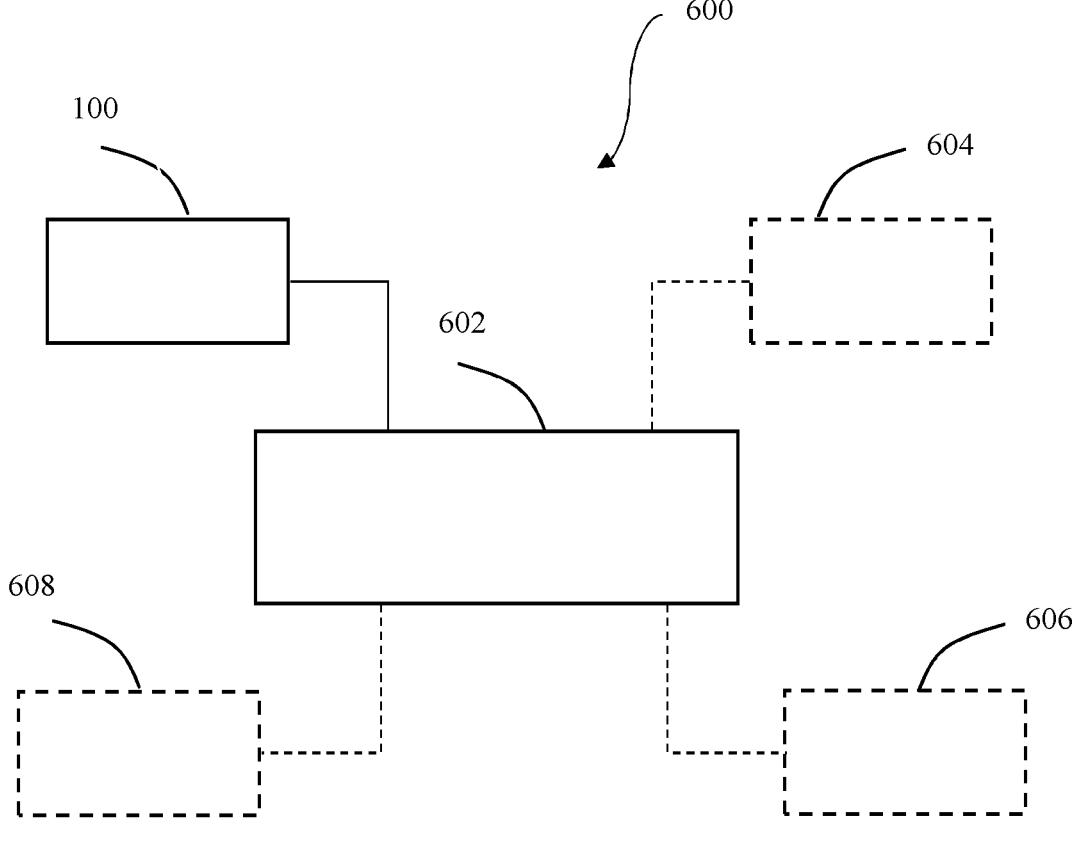
FIG. 6 depicts a system according to an embodiment.

FIG. 6 illustrates a system 600 for quantitatively detecting a biomarker in a sweat sample from a subject according to an embodiment. System 600 comprises a device 100, such as is described previously. It will be understood that device 100 of the system of FIG. 6 could be any device as described herein, including for example any of the devices depicted in any of FIGS. 1 to 4. System 600 also comprises a processor 602, configured as described herein to acquire data relating to the concentration of the marker in the carrier fluid from the first sensor, and may comprise one or more of the following elements: a physiological sensor 604, a memory 606 and/or a user interface 608, each of which may for example be as described herein. In some embodiments, the device 100 itself may comprise the processor 602 and one or more of one or more of the following elements: a physiological sensor 604, a memory 606 and/or a user interface 608. Alternatively or in addition, in some embodiments, processor 602 or a second processor may be external to (e.g. separate to or remote from) the device 100. In these embodiments, the processor can be communicatively coupled to the device 100.

Although reference is made to "a" processor, it will be understood that the processor may comprise one or more processors. The one or more processors can be implemented in numerous ways, with software and/or hardware, to perform the various functions described herein. In some embodiments, each of the one or more processors can be configured to perform individual or multiple steps of the method described herein. In particular implementations, the one or more processors can comprise a plurality of software and/or hardware modules, each configured to perform, or that are for performing, individual or multiple steps of the method described herein. The one or more processors may comprise one or more microprocessors, one or more multi-core processors and/or one or more digital signal processors (DSPs), one or more processing units, and/or one or more controllers (such as one or more microcontrollers) that may be configured or programmed (e.g. using software or computer program code) to perform the various functions described herein. The one or more processors may be implemented as a combination of dedicated hardware (e.g. amplifiers, pre-amplifiers, analog-to-digital convertors (ADCs) and/or digital-to-analog convertors (DACs)) to perform some functions and one or more processors (e.g. one or more programmed microprocessors, DSPs and associated circuitry) to perform other functions.

In some embodiments, processor 602 is configured to control operation of one or pumps and valves of a device such as described herein in order to perform one or more methods as described herein.

In some embodiments, processor 602 is configured to: acquire data from the first sensor of the wearable device; acquire data from the second sensor of the wearable device; and determine the concentration of the biomarker in the sweat sample based on the data from the first and second sensors.

In some embodiments, the data acquired from the first sensor comprises concentration of the marker in the carrier fluid and the processor is configured to determine sweat flow rate based on the concentration of the marker in the carrier fluid.

In some embodiments, processor 602 is configured to determine the flow rate of one or both of the carrier fluid and the sweat sample based on the acquired data from the first sensor. In some embodiments, the concentration of the biomarker in the sweat sample is determined based on the flow rate of one or both of the carrier fluid and the sweat sample.

In some embodiments, processor 602 is configured to determine a sweat dilution factor, from which the sweat flow rate can be determined. The sweat flow rate is relevant since for particular biomarkers the concentration in sweat as measured by the second sensor depends on the average sweat rate per gland. In some embodiments, processor 602 is configured to compare acquired and/or determined data to a corresponding set of data in a look up table and determine if the measured biomarker concentration is caused by an illness or just by a change in sweat rate.

In some embodiments, the system may comprise a physiological sensor 604, such as are described above in connection with the method. Such sensors allow for monitoring of other factors that can affect sweat flow rate or be indicative of changes in sweat flow rate, such as vital sign sensors, accelerometers and pH sensors.

In some embodiments, the system may comprise a communications interface (or communications circuitry). In some embodiments, the device described earlier may comprise a communications interface. Alternatively or in addition, the communications interface may be external to (e.g. separate to or remote from) the device. The communications interface can be for enabling the device, or components of the device, to communicate with and/or connect to one or more other components of the system (e.g. one or more sensors, interfaces, devices, processors, or memories), such as any of those described herein. For example, the communications interface can be for enabling the device (or one or more components of the device, such as the first and second sensors) to communicate with and/or connect to a processor (such as that mentioned earlier).

The communications interface may enable the device, or components of the device, to communicate and/or connect in any suitable way. For example, the communications interface may enable the device, or components of the device, to communicate and/or connect wirelessly, via a wired connection, or via any other communication (or data transfer) mechanism. In some wireless embodiments, for example, the communications interface may enable the device, or components of the device, to use radio frequency (RF), Bluetooth, or any other wireless communication technology to communicate and/or connect.

In some embodiments, the system may comprise at least one memory 606. In some embodiments, the device described earlier may comprise at least one memory. Alternatively or in addition, at least one memory 606 may be external to (e.g. separate to or remote from) the device. For example, a hospital database may comprise the memory, the memory may be a cloud computing resource, or similar. The device (or a processor of the system) may be configured to communicate with and/or connect to at least one memory. A memory may comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM), and electrically erasable PROM (EEPROM). In some embodiments, at least one memory can be configured to store program code that can be executed by a processor (such as a processor of the device) to cause the device to operate in the manner described herein.

Alternatively or in addition, in some embodiments, at least one memory can be configured to store information required by or resulting from the method described herein. For example, in some embodiments, at least one memory may be configured to store any one or more of: data acquired by any of the sensors described herein, data relating to the predetermined concentration of the marker in the carrier fluid, or the pre-determined (or adapted) flow rate of the carrier fluid, or one or more look-up tables correlating sweat flow rate and biomarker concentration as indicators of physiological status, or any other information, or any combination of information, required by or resulting from the method described herein. In some embodiments, the device (or a processor of the system) can be configured to control at least one memory to store information required by or resulting from the method described herein.

The system may comprise a user interface 608. In some embodiments, the device described earlier may comprise the user interface. Alternatively or in addition, the user interface may be external to (e.g. separate to or remote from) the device. The device (or a processor of the system) may be configured to communicate with and/or connect to a user interface. In some embodiments, the device (or a processor of the system) can be configured to control the user interface to operate in the manner described herein.

The user interface 608 can be configured to render (or output, display, or provide) information required by or resulting from the method described herein. For example, in some embodiments, the user interface may be configured to render (or output, display, or provide) one or more of: data acquired by any of the sensors described herein, data relating to the predetermined concentration of the marker in the carrier fluid, or the pre-determined (or adapted) flow rate of the carrier fluid, or one or more look-up tables correlating sweat flow rate and biomarker concentration as indicators of physiological status, or any other information, or any combination of information, required by or resulting from the method described herein. Alternatively or in addition, the user interface 608 can be configured to receive a user input. For example, the user interface 608 may allow a user to manually enter information or instructions, interact with and/or control the device 100. Thus, the user interface may be any user interface that enables the rendering (or outputting, displaying, or providing) of information and, alternatively or in addition, enables a user to provide a user input.

For example, the user interface may comprise one or more switches, one or more buttons, a keypad, a keyboard, a mouse, a touch screen or an application (for example, on a smart device such as a tablet, a smartphone, or any other smart device), a display or display screen, a graphical user interface (GUI) such as a touch screen, or any other visual component, one or more speakers, one or more microphones or any other audio component, one or more lights (such as light emitting diode LED lights), a component for providing tactile or haptic feedback (such as a vibration function, or any other tactile feedback component), an augmented reality device (such as augmented reality glasses, or any other augmented reality device), a smart device (such as a smart mirror, a tablet, a smart phone, a smart watch, or any other smart device), or any other user interface, or combination of user interfaces. In some embodiments, the user interface that is controlled to render information may be the same user interface as that which enables the user to provide a user input.

There is also provided a computer program product comprising a computer readable medium. The computer readable medium has computer readable code embodied therein. The computer readable code is configured such that, on execution by a suitable computer or processor, the computer or processor is caused to perform the method described herein. The computer readable medium may be, for example, any entity or device capable of carrying the computer program product. For example, the computer readable medium may include a data storage, such as a ROM (such as a CD-ROM or a semiconductor ROM) or a magnetic recording medium (such as a hard disk). Furthermore, the computer readable medium may be a transmissible carrier, such as an electric or optical signal, which may be conveyed via electric or optical cable or by radio or other means. When the computer program product is embodied in such a signal, the computer readable medium may be constituted by such a cable or other device or means. Alternatively, the computer readable medium may be an integrated circuit in which the computer program product is embedded, the integrated circuit being adapted to perform, or used in the performance of, the method described herein.

There is thus provided herein an improved device 100, 200, 300, 400, method 500, system 600, and computer program product for quantitatively detecting a biomarker in a sweat sample obtained from the skin of a subject, which addresses the limitations associated with the existing techniques. The devices, methods and systems described herein can be used in the field of patient monitoring as an early warning for sudden deterioration of patients in the General Ward and ICU, and for investigation of sleep disorders, as currently measurements are only done in a spot-check fashion when a patient is visiting a doctor.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A wearable device for quantitatively detecting a biomarker in a sweat sample obtained from skin of a subject, the device comprising:

a microfluidic network comprising:

a reservoir filled with a carrier fluid containing a predetermined amount of a marker;

a sample collection chamber disposed downstream from the reservoir and adapted to contact the skin of the subject and collect a sweat sample;

a first sensor disposed downstream from the sample collection chamber and adapted to detect the marker, wherein the first sensor is adapted to measure concentration of the marker in the carrier fluid; and a second sensor disposed downstream from the first sensor and adapted to detect the biomarker, wherein the microfluidic network further comprises a recirculation channel extending from a section of the microfluidic network downstream from the first and second sensors to a section of the microfluidic network intermediate to the reservoir and the sample collection chamber.

2. The device of claim 1, wherein a membrane which is selective for the biomarker is disposed downstream from the sample collection chamber and upstream of the first sensor.

3. The device of claim 1, wherein the device is configured to detect the biomarker at a sweat flow rate of between 0.03 and 20 nL/min/gland.

4. The device of claim 1, wherein the marker comprises at least one of a dye, an inert colloidal particle, or an electrochemically detectable compound of predetermined concentration.

5. The device of claim 1, further comprising one or more pumps configured to pump the carrier fluid at a predetermined flow rate of from 10 nL/min to 60 nL/min.

6. A method of using the wearable device of claim 1 in contact with skin of the subject to quantitatively detect the biomarker in the sweat sample from the subject, the method comprising:

pumping the carrier fluid containing the marker to the sample collection chamber of the wearable device, wherein the sample collection chamber is adapted to contact the skin of the subject and collect the sweat sample;

pumping the carrier fluid containing the marker and the sweat sample from the sample collection chamber to the first and second sensors;

acquiring data relating to concentration of the marker present in the carrier fluid from the first sensor;

acquiring data relating to the biomarker from the second sensor;

determining the concentration of the biomarker in the sweat sample based on the data from the first and second sensors, and determining sweat flow rate based on the concentration of the marker in the carrier fluid.

7. The method of claim 6, comprising:

determining a flow rate of one or both of the carrier fluid and the sweat sample based on the acquired data from the first sensor.

8. The method of claim 6, comprising:

determining a concentration of the biomarker in the sweat sample based on the flow rate of one or both of the carrier fluid and the sweat sample.

9. The method of claim 6, wherein the biomarker comprises one or more of: Na+, K+, Cl−, urea, ethanol, glucose, lactate ions, ammonium ions or cortisol.

10. The method of claim 6, comprising:

acquiring physiological data on the subject from a physiological sensor; and adjusting a flow rate of the carrier fluid based on the acquired physiological data.

11. A system for quantitatively detecting a biomarker in a sweat sample obtained from skin of a subject, the system comprising:

a wearable device as claimed in claim 1; and a processor configured to:

acquire data from the first sensor of the wearable device, wherein the data acquired from the first sensor comprises concentration of the marker in the carrier fluid;

acquire data from the second sensor of the wearable device; and determine the concentration of the biomarker in the sweat sample based on the data from the first and second sensors, and wherein the processor is configured to determine sweat flow rate based on the concentration of the marker in the carrier fluid.

12. A computer program product comprising a non-transitory computer readable medium, the non-transitory computer readable medium having computer readable code embodied therein, the computer readable code being configured such that, on execution by a computer or a processor, the computer or processor is caused to perform the method as claimed in claim 6.

* * * * *